US008530599B2

(12) United States Patent
Rowell

(10) Patent No.: US 8,530,599 B2
(45) Date of Patent: *Sep. 10, 2013

(54) HYDROPHOBIC SILICA PARTICLES AND METHODS OF MAKING SAME

(75) Inventor: Frederick John Rowell, Durham (GB)

(73) Assignee: University of Sunderland, Sunderland (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,011

(22) Filed: Sep. 26, 2011

(65) Prior Publication Data

US 2012/0014858 A1  Jan. 19, 2012

Related U.S. Application Data

(63) Continuation of application No. 11/501,054, filed on Aug. 9, 2006, now Pat. No. 8,026,328.

(60) Provisional application No. 60/706,439, filed on Aug. 9, 2005, provisional application No. 60/706,438, filed on Aug. 9, 2005, provisional application No. 60/795,599, filed on Apr. 28, 2006, provisional application No. 60/831,204, filed on Jul. 17, 2006.

(30) Foreign Application Priority Data

Aug. 9, 2005 (GB) .................................. 0516271.4
Aug. 9, 2005 (GB) .................................. 0516272.2
Apr. 28, 2006 (GB) .................................. 0608464.4
May 26, 2006 (GB) .................................. 0610453.3

(51) Int. Cl.
*C08G 77/00* (2006.01)

(52) U.S. Cl.
USPC ............ 528/10; 427/1; 427/157; 252/301.16; 252/88.2; 252/408.1

(58) Field of Classification Search
None
See application file for complete search history.

(56) References Cited

U.S. PATENT DOCUMENTS

| 3,075,852 A | | 1/1963 | Bonora |
| 3,492,140 A | * | 1/1970 | Tsuyuki et al. .................... 427/1 |
| 4,176,205 A | | 11/1979 | Molina |
| 4,837,260 A | * | 6/1989 | Sato et al. ..................... 524/261 |
| 5,102,763 A | * | 4/1992 | Winnik et al. ........... 430/108.24 |
| 5,204,088 A | | 4/1993 | Noebel et al. |

(Continued)

FOREIGN PATENT DOCUMENTS

| EP | 1369907 A2 | 12/2003 |
| JP | 63184056 A | 7/1988 |

(Continued)

OTHER PUBLICATIONS

Zhang et al. J. Phys. Chem. B, 2001, 105(29), 6755-6758.*

(Continued)

*Primary Examiner* — Robert S Loewe
(74) *Attorney, Agent, or Firm* — Myers Bigel Sibley & Sajovec, P.A.

(57) ABSTRACT

A method of preparing hydrophobic silica particles includes the step of reacting together in a single step a mixture of silane ether monomers and organically modified silane ether monomers with a hydrolyzing agent. The method also includes producing hydrophobic silica microparticles and nanoparticles that can include dyes and/or magnetizable components. The silica nanoparticles can be used in the detection, visualization and/or analysis of latent fingerprints.

33 Claims, 9 Drawing Sheets

(56) References Cited

U.S. PATENT DOCUMENTS

| | | | |
|---|---|---|---|
| 5,209,998 A * | 5/1993 | Kavassalis et al. | 430/108.7 |
| 5,272,240 A * | 12/1993 | Haruvy et al. | 528/10 |
| 5,683,501 A * | 11/1997 | Tomihisa et al. | 106/491 |
| 5,758,797 A * | 6/1998 | Martindale | 220/719 |
| 6,048,546 A | 4/2000 | Sasaki et al. | |
| 6,174,512 B1 * | 1/2001 | Kosuge et al. | 423/705 |
| 6,194,213 B1 | 2/2001 | Barbera-Guillem | |
| 6,299,674 B1 | 10/2001 | Takamura et al. | |
| 6,306,662 B1 | 10/2001 | Menzel | |
| 6,495,352 B1 | 12/2002 | Brinker et al. | |
| 6,743,558 B2 | 6/2004 | Yamaguchi et al. | |
| 7,258,874 B2 | 8/2007 | Barbe et al. | |
| 7,754,646 B2 * | 7/2010 | Trau et al. | 502/233 |
| 7,976,585 B2 * | 7/2011 | Cremer et al. | 8/405 |
| 8,026,328 B2 | 9/2011 | Rowell | |
| 2002/0001716 A1 | 1/2002 | Barbera-Guillem | |
| 2002/0055051 A1 | 5/2002 | Kudo et al. | |

FOREIGN PATENT DOCUMENTS

| | | |
|---|---|---|
| WO | 01/62232 A1 | 8/2001 |
| WO | 03/083481 A2 | 10/2003 |
| WO | 2004/063387 A2 | 7/2004 |
| WO | 2005/066632 A1 | 7/2005 |

OTHER PUBLICATIONS

Sodhi et al. Foresnsic Science International, 2001, 120, 172-176.*

Nicolaides "Skin Lipids: Their Biochemical Uniqueness", *Science* 186:19-26 (1974).

Sumio Sakka, Handbook of Sol-Gel Science and Technology: Processing Characterization and Applications, Nov. 2004, Springer, I edition, pp. 34-35.

Arun Wagh, Chemically Bonded Phosphate Ceramics: Twenty-First Century Materials with Diverse Applications, Jan. 2005, Elsevier Science, p. 135.

Fred S. Miller, Brian D. Andresen: Aerogel Fingerprint Media: Sep. 1999; Office of Scientific and Technical Information (OSTI); pp. 1-21.

Balachandran, U., Gubser, D.U. Hartwig, K.T. Bardos, V.A: Advances in Cryogenic Engineering (The Effect of Nanostructure on the Thermal Behavior of Aerogels), 2000, Kluwer Academic/Plenum; vol. 46, pp. 345-347 and 349.

Omnichrome Spectrum 9000 Cagalog.

Rovelyn Tapec, Xiaojun Julia Zhao, Weihong Tan; Development of Organic Dye-Doped Silica Nanoparticles for Bioanalysis and Biosensors; 2002; American Scientific Publishers; Vo. 2, No. 3/4, pp. 405-409.

AEROSIL 972 data sheet, no date.

International Search Report for PCT/GB2006/050233.

Written Opinion of the International Searching Authority for PCT/GB2006/050233.

A. V. Rao, et al., "Synthesis and Characterization of Hydrophobic Silica Aerogels Using Trimethylethoxysilane as a Co-Precursor", Journal of Sol-Gel Science and Technology, vol. 27, 2003, pp. 103-109 (XP-002404003).

Transmittal; International Search Report; and the Written Opinion for International Application PCT/GB2005/000038 with a mailing date of Jun. 13, 2005.

C. Champod, C. Lennard, P. Margot, and M. Stoilovic, in Fingerprints and Other Ridge Skin Impressions, CRC Press, Boca Raton, (2004), (Ch. 4, Appxs 3 & 4).

G.S. Sodhi and J. Kaur, "Powder Method for Detecting Latent Fingerprints: A Review", Forensic Sci. Int., 120, (2001), pp. 172-176.

E.R. Menzel, S.M. Savoy, S.J. Ulvick, K.H. Cheng, R.H. Murdock, and M.R. Sudduth, "Photoluminescent Semiconductor Nanocrystals for Fingerprint Detection", Journal of Forensic Sciences, (1999), pp. 545-551.

E.R. Menzel, M. Takatsu, R.H. Murdock, K. Bouldin, and K.H. Cheng, "Photoluminescent CdS/Dendrimer Nanocomposites for Fingerprint Detection", Journal of Forensic Sciences, (2000), pp. 770-773.

E.R. Menzel, "Functionalized Europium Oxide Nanoparticles for Fingerprint Detection—A Preliminary Study", J. Forensic Ident., vol. 55, Issue 2, Mar./Apr. 2005, pp. 189 to 195.

Expert Group on Vitamins and Minerals Secretariat, "Review of Silican", Aug. 2002.

L.A. Harris, J.D. Goff, A.Y. Carmichael, and J.S. Riffle, "Magnetite Nanoparticle Dispersions Stabilized by Triblock Copolymers", Chemistry of Materials, 15, (2003), p. 1367.

* cited by examiner

Ethidium Bromide (A)

Bromothymol Blue (B)

Rhodamine B (C)

Rhodamine 6G (D)

Sodium Fluorescein (E)

Crystal Violet (F)

(A)

(B)

(C)

(D)

(A)  (B)

HYDROPHOBIC SILICA PARTICLES AND METHODS OF MAKING SAME

RELATED APPLICATIONS

This application is a continuation of U.S. Patent Application No 11/501,054, filed on Aug. 9, 2006, now .U.S. Pat. No. 8,026,328, issued on Sep. 27, 2011, which claims priority under 35 U.S.C. §119(e) to U.S. Provisional Application No. 60/706,439, filed on Aug. 9, 2005, U.S. Provisional Application No. 60/706,438, filed on Aug. 9, 2005, U.S. Provisional Application No. 60/795,599, filed on Apr. 28, 2006, and U.S. Provisional Application No. 60/831,204, filed on Jul. 17, 2006, the entire contents of each of which are hereby incorporated by reference herein. This application also claims priority under 35 U.S.C. §119 to Great Britain Patent Application No. 0514272.2, filed on Aug. 9, 2005, Great Britain Patent Application No. 0516271.4, filed on Aug. 9, 2005, Great Britain Patent Application No. 0608464.4, filed on Apr. 28, 2006, and Great Britain Patent Application No. 0610453.3, filed on May 26, 2006, the entire contents of each of which are hereby incorporated by reference herein.

BACKGROUND

1. Field of the Invention

The present invention relates to a method of synthesizing blank and doped hydrophobic silica particles and the use of these particles in, for example, fingerprinting and other applications.

2. Background Information

The development of latent fingerprints generally involves either the use of a dusting agent that adheres to the "sticky" material deposited on the surface following contact, or a chemical developer that produces a visual coloration due to chemical interaction of the applied developer with chemicals commonly found within the deposited materials on the surface, as described in, for example, Champod, C., Lennard, C., Margot, P. and Stoilovic, M., in *Fingerprints and Other Ridge Skin Impressions*, CRC Press, Boca Raton, 2004 (ISBN 0-415-27175-4) (hereinafter, the "Champod et al. reference"). The size and shape of the powder particles have a large influence on the amount of adhesion they have to the fingerprint, and fine particles tend to adhere better than larger particles, thus resulting in most particles being based on particle sizes of 1-10M, as described in, for example, G. S. Sodhi and J. Kaur, "Powder Method for Detecting Latent Fingerprints: A Review," Forensic Sci. Int., 120 (2001), pages 172-176 (hereinafter, the "Sodhi et al. reference"). A range of dusting agents are commercially available that are based on a variety of particles, both naturally occurring and synthetic, that show affinity for the hydrophobic materials within the deposited print.

With recent innovations in nanotechnology, potential alternative approaches have been studied. Cadmium sulphide and Europium (III) oxide based powders have been used to visualize latent fingerprints, as described in, for example: E. R. Menzel, S. M Savoy, S. J. Ulvick, K. H. Cheng, R. H. Murdock and M. R. Sudduth, "Photoluminescent Semiconductor Nanocrystals for Fingerprint Detection," Journal of Forensic Sciences (1999), pages 545-551 (hereinafter, the "first Menzel et al. reference"); E. R. Menzel, M. Takatsu, R. H. Murdock, K. Bouldin and K. H. Cheng, "Photoluminescent CdS/Dendrimer Nanocomposites for Fingerprint Detection," Journal of Forensic Sciences (2000), pages 770-773 (hereinafter, the "second Menzel et al. reference"); and E. R. Menzel, "Functionalized Europium Oxide Nanoparticles for Fingerprint Detection—A Preliminary Study," J. Forensic Ident. (hereinafter, the "Menzel reference"). However, these methods are complex and require specialist technical development and expensive instruments, and, hence, are unsuitable to be used in situ, for example, at scenes of crime.

Two reports describe the use of combinations of tetraethoxysilane (TEOS) and phenyltriethoxysilane (PTEOS) to produce relatively hydrophobic silica aerogels (see the first Menzel et al. reference) and the corresponding nanoparticles (see the second Menzel et al. reference) for use in bioanalysis and biosensor applications. The former report demonstrated that as the proportion of PTEOS increased, the hydrophobicity of the resulting sol gel also increased, while the latter report used the particles' hydrophobicity to incorporate the hydrophobic dye, rhodamine 6G, into the resulting particles. The nanoparticles were highly fluorescent with the dye being strongly retained within the particles under aqueous conditions. However, these particles are synthesized using a multi-step route.

SUMMARY OF THE INVENTION

A novel, single-step synthetic route has now been developed for producing hydrophobic silica particles. Such a synthetic route is simpler and can be applied to the production of a variety of micro or nanoparticles that optionally incorporate dyes (for example, colored or fluorescent) and magnetic or paramagnetic subparticles into the silica monomer backbone.

Such an approach overcomes problems arising from direct incorporation of fluorescent or colored molecules into the particles during their synthesis, or their sol gel equivalents, since the resulting particles or gels generally lose the dyes when the particles are washed. This observation implies that there are only weak interactions between embedded molecules within the crossed linked silicate backbone of the particles' matrix so that dye molecules are not subjected to attractive forces that would retain them within the matrix.

The present invention has also demonstrated the use of these hydrophobic silica micro- and nanoparticles as developing agents for latent fingerprints.

Thus, exemplary embodiments of the present invention are directed to a method for preparing hydrophobic silica particles, the method comprising reacting together in a single step a mixture of (I) silane ether monomers, for example, an alkoxysilane and (2) organically substituted silane ether monomers, for example, a phenyl modified silane ether, and (3) a hydrolyzing agent.

In one exemplary embodiment, the hydrolyzing agent comprises an alkali.

Thus, the method can comprise the use of an alkoxysilane, particularly tetraalkoxysilanes (abbreviated herein to TAOS). The TAOS's can be selected from TEOS (tetraethoxysilane) or TMOS (tetramethoxysilane).

The method can involve the use of a hydrocarbyl-substituted, particularly an aryl-substituted silane ether, e.g., a silane ether in which one or two of the ether forming groups (RO—) are each replaced by an aryl-containing group, e.g., a phenyl group.

Thus, exemplary substituted silane ethers can be of the formula $(R'O)_m(R_2)_n Si$, where R' is an organic residue, $R^2$ is an aryl-containing group and m is 2 or 3, while n is 1 or 2, provided that (n+m)=4.

In one exemplary embodiment of the present invention, there is provided a method for preparing hydrophobic silica particles, the method comprising reacting together in a single step a mixture of TEOS (tetraethoxysilane) and PTEOS (phenyltriethoxysilane) monomers with a hydrolyzing agent.

In a further exemplary embodiment of the present invention, there is provided a method for preparing hydrophobic silica particles, the method comprising reacting together in a single step a mixture of TEOS and PTEOS monomers with an alkali.

In a further exemplary embodiment of the present invention, there is provided a method for preparing hydrophobic silica particles, the method comprising reacting together in a single step a mixture of (i) TEOS (tetraethoxysilane) or TMOS (tetramethoxysilane) monomers, or a combination thereof, and (ii) PTEOS (phenyltriethoxysilane) monomers with a hydrolyzing agent, e.g., an alkali.

The hydrolyzing agent, e.g., an alkali, acts as a catalyst for the reaction between the silane ether monomers, for example, TEOS, and the organically substituted silane ether monomers, for example PTEOS.

In exemplary embodiments of the present invention, the method comprises incorporating functional agents for imparting post-manufacture functions. The functional agents can aid in the detection, imaging and handling of the particles. For example, dye molecules, other visualizing agents and/or magnetic particles can be incorporated into the silica particles. The addition of dye molecules and/or other visualizing agents aids in the visualization of fingerprints. The addition of magnetic (or magnetizable) particles can aid in the handling of the particles, as described in more detail later.

In a further aspect of the present invention, there are provided hydrophobic silica microparticles obtainable by the methods of the present invention. Also provided by the present invention are hydrophobic silica nanoparticles obtainable (having the characteristics of a product obtained) by the methods of the present invention. In one exemplary embodiment of the present invention, there are provided hydrophobic silica microparticles that are coalesced silica nanoparticles.

In one exemplary embodiment, a method is provided for producing hydrophobic silica microparticles from silica nanoparticles, wherein the method comprises providing conditions suitable for the nanoparticles to aggregate to form silica microparticles. For example, the method can comprise drying of the nanoparticles to encourage coalescing.

Also included according to exemplary embodiments of the present invention is the use of hydrophobic silica particles for detecting fingerprints, whether direct or lifted from a surface.

In a further aspect of the present invention, there is provided a method of detecting a fingerprint, either on a surface or lifted from a surface, that comprises contacting an agent comprising hydrophobic silica particles with a fingerprint. The method can optionally comprise imaging the particles when applied to, or contained as part of, a fingerprint.

According to a first aspect of the present invention, a method of preparing hydrophobic silica particles includes the step of: (a) reacting together in a single step a mixture of silane ether monomers and organically modified silane ether monomers with a hydrolyzing agent.

According to the first aspect, the silane ether monomers can comprise tetraalkoxysilane monomers or the like. The method can include the step of: (b) reacting together in a single step a mixture of triethoxysilane and phenyltriethoxysilane monomers with the hydrolyzing agent. The silane ether monomers can comprise tetramethoxysilane monomers. The hydrolyzing agent can comprise an acid. Alternatively, the hydrolyzing agent can comprise an alkali. For example, the alkali can comprise a hydroxide, such as, for example, ammonium hydroxide. Dye molecules and/or colored particles can be included in the mixture of the monomers and the hydrolyzing agent, whereby the dye molecules and/or the colored particles are incorporated into the hydrophobic silica particles. The dye molecules and/or the colored particles can comprise one of rhodamine B, rhodamine 6G, carbon black, titanium dioxide, magnetite, crystal violet, and methylene blue.

According to the first aspect, magnetic and/or paramagnetic particle can be included in the mixture of the monomers and the hydrolyzing agent, whereby the magnetic and/or the paramagnetic particles are incorporated into the hydrophobic silica particles. The monomers can comprise triethoxysilane monomers and phenyltriethoxysilane monomers. For example, haematite, titanium dioxide, carbon black and/or magnetite can be included in the mixture of monomers. The method can include the steps of: (c) centrifuging a reaction product containing hydrophobic silica particles obtained from step (a); (d) suspending the reaction product in an aqueous phase; (e) extracting the reaction product from the aqueous phase into an organic phase; (f) evaporating the organic phase; and (g) crushing and sieving the product obtained in step (f) to form hydrophobic silica microparticles. The organic phase can comprise a non-polar solvent or a solvent with a low polarity, such as, for example, dichloromethane. The microparticles can comprise an average diameter of from about 0 to about 90 μm. Alternatively, the microparticles can comprise an average diameter of from about 45 to about 65 μm. However, the microparticles can comprise an average diameter of from about 65 to about 90 μm.

According to the first aspect, the method can include the step of: (h) suspending a reaction product comprising hydrophobic silica particles obtained from step (a) in an aqueous:solvent solution to form a suspension of hydrophobic nanoparticles. The method can include the step of: (i) drying the particles to encourage aggregation of the particles to form microparticles. The nanoparticles can comprise an average diameter of about 200 to about 900 nm. Alternatively, the nanoparticles can comprise an average an average diameter from about 300 to about 600 nm. However, the nanoparticles can comprise an average diameter of about 400 to about 500 nm. The reaction product can be centrifuged prior to suspension. The aqueous:solvent mixture can comprises a first aqueous:solvent mixture comprising between about 60 (aqueous):40 (solvent): and about 40:60 mixture.

According to the first aspect, the method can include the steps of: (j) suspending the hydrophobic silica particles in a fluid, centrifuging the suspension, and collecting the particles; and (k) resuspending in a fluid, recentrifuging and recollecting the particles. The method can include the step of: (l) repeating step (k) at least once, whereby hydrophobic nanoparticles are suspended. The fluid can comprise a mixture comprising water and an organic solvent. The organic solvent can comprise a water-miscible solvent. The organic solvent can comprise ethanol. An initial fluid can comprise a mixture of water and organic solvent at a ratio of from about 60 (water):40 (solvent) to about 40:60 mixture. The proportion of solvent in the mixture can be increased between the initial suspension of step (b) and a final suspension. At least two steps of resuspending, recentrifuging and recollecting from step (k) can be performed, and the substantially same mixture is used in the first resuspension as in the initial suspension. The silane ether can comprise triethoxysilane, the organically modified silane ether can comprise phenyltriethoxysilane, and the ratio of triethoxysilane:phenyltriethoxysilane can comprise about 1:1 v/v.

According to a second aspect of the present invention, the hydrophobic silica particle can be used as an agent for detecting hydrophobic area or deposit, e.g., a latent fingerprint; on a surface. The hydrophobic silica particles can be obtainable by the method of step (a) above. Hydrophobic silica particles can be applied to the surface within a dust or a suspension. The suspension can comprise an ethanolic aqueous suspension. The silica particles can comprise a dye molecule and/or a colored particle for imaging the particles when applied to the surface of a fingerprint. The particles can comprise microparticles and comprise an average diameter of about between about 10 and about 90 µm, optionally from about 45 and about 65 µm and further optionally from about 65 and about 90 µm, wherein optionally the microparticles can be included in a dusting agent for contacting with a fingerprint. Alternatively, the particles can comprise nanoparticles and comprise an average diameter of about from about 100 and 900 nm, optionally from about 300 and 600 nm and further optionally from about 400 to 500 nm, wherein optionally the agent comprising the nanoparticles is an ethanolic aqueous suspension.

According to a third aspect of the present invention, a method for detecting and/or identifying a fingerprint or other hydrophobic mass or deposit includes the step of: (1) contacting an area where there is or maybe a fingerprint with an agent comprising hydrophobic silica particles. The silica particles can be obtainable by a method according to step (a) above. The method can include the step of: (2) visualizing or imaging the fingerprints. The silica particles can comprise a visualization or imaging agent and the method can include the step of: (3) visualizing and/or imaging the particles after the surface has been contacted with them. The particles can comprise a dye molecule for imaging the fingerprint. The particles can comprise a magnetic or paramagnetic particle that enables the agent to be applied to the area using a magnetic applicator. The method can include the step of: (4) visualizing the fingerprints using an optical method, optionally wherein the optical method comprises one of a UV search light, an optical scanner including a flat-bed optical scanner, a fluorescent scanner and a UV visible scanner.

According to a fourth aspect of the present invention, a hydrophobic silica particle can be obtainable by a method according to step (a) above, e.g., a particle comprising an average diameter of from about 200 nm to about 900 nm or from about 10 µm and about 90 µm.

According to a fifth aspect of the present invention, a hydrophobic silica particle can comprise a dye molecule and include one or more of the following features: (i) a magnetizable or paramagnetizable particle; (ii) it is a microparticle that is a coalescence of smaller nanoparticles, wherein the microparticle comprises an average diameter of between about 10 µm and about 90 µm; or (iii) it is a nanoparticle that comprises an average diameter from about 200 nm to about 900 nm.

According to a sixth aspect of the present invention, a method for making silica microparticles comprising a diameter of at least about 10 µm includes the steps of: (i) making hydrophobic nanoparticles comprising an average particle size of about 500 nm+/−100 nm in diameter; and (ii) causing or allowing the nanoparticles to coalesce into microparticles each comprising a diameter of at least about 5 µm. Step (ii) can comprise the step of: (iii) causing or allowing the nanoparticles to coalesce into microparticles each comprising a diameter of at least about 20 µm. Alternatively, step (ii) can comprise the step of: (iv) causing or allowing the nanoparticles to coalesce into microparticles each comprising a diameter of at least about 25 to 30 µm.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein.

DETAILED DESCRIPTION OF THE PREFERRED EMBODIMENTS

Method A

Figure 1:
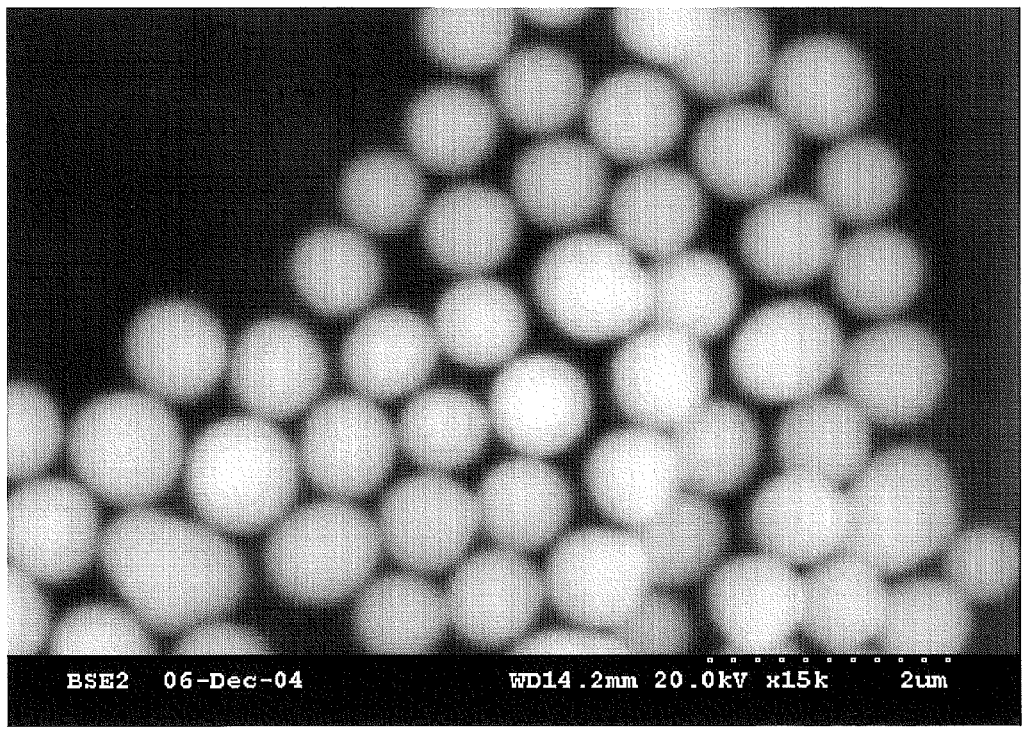
FIG. 1 is a picture taken by a scanning electron microscope of carbon black embedded nanoparticles, in accordance with an exemplary embodiment of the present invention.

A method for preparing hydrophobic silica particles is provided that comprises the step of reacting together in a single step a mixture of (1) silane ether monomers, for example, a alkoxysilane, and (2) organically substituted silane ether monomers, for example a phenyl modified silicate, with a hydrolyzing agent, e.g., an alkali.

Thus, the method according to an exemplary embodiment can comprise the use of alkoxysilane monomers. The method can comprise the use of tetraalkoxysilanes (abbreviated herein to "TAOS"). The TAOS's are can be selected from TEOS (tetraethoxysilane) or TMOS (tetramethoxysilane) or the like.

In one exemplary embodiment, the method can comprise the step of reacting together in a single step a mixture of TEOS (tetraethoxysilane) and PTEOS (phenyltriethoxysilane) monomers with a hydrolyzing agent. Alternatively, TMOS can be used in place of TEOS in the method.

In one exemplary embodiment, the method can comprise the step of reacting TMOS monomers and PTEOS monomers.

In one exemplary embodiment, the mixture further comprises a water miscible solvent, for example, ethanol, and water.

In one exemplary embodiment, the method can be carried out at ambient temperature. The duration of the reaction is not critical. In one exemplary embodiment, the reaction between the TAOS monomers and PTEOS monomers can be performed overnight or for an equivalent time period, that is to say for between about 12 and about 18 hours. The length of the reaction has an effect on the size of silica particles produced. For example, the earlier a reaction is stopped, the smaller are the particles that are formed. In other exemplary embodiments, therefore, the reaction can be performed over a period of less than 12 hours, e.g., between about 6 and about 12 hours. In yet other exemplary embodiments, the reaction can be performed for longer than about 18 hours. If desired, the temperature can be elevated (or reduced) and the duration of the reaction reduced (or increased).

The hydrolyzing agent, typically an alkali, acts as a catalyst within the reaction. Preferably, this catalyst is a hydroxide, for example, ammonium hydroxide. In other exemplary embodiments, the catalyst can be an acid or the like. Examples of acids include, but are not limited to, mineral acids, e.g., hydrochloric acid. In this exemplary embodiment, the reaction comprises an acid induced hydrolysis.

The silane ether monomer, for example, a TAOS, and the organically substituted silane ether monomer, e.g., PTEOS monomers, can be used, for example, in ratios (PTEOS:TAOS) of from about 2:1 to about 1:2, e.g., about 4:3 to about 3:4, and, in particular, about 1.2:1 to about 1:1.2. In one class of methods, the ratio is at least about 1:1, e.g., up to about 1:5, for example, about 1:2. In one class of methods, the PTEOS:TAOS ratio is preferably 1:1 v/v. It will be understood by skilled artisans that, where one or both of the TAOS and PTEOS are replaced by alternative reagents, the same ratios can be used.

In a further exemplary embodiment of the present invention, there is provided a method for isolating hydrophobic silica particles from a reaction medium formed from the reaction of Method A.

Particles produced by the above method tend to be predominantly nanoparticles, that is to say, of an average diameter of approximately 200 nm to about 900 nm, typically about 300 nm to about 800 nm and particularly about 400 nm to about 500 nm. These nanoparticles can be subsequently processed to form microparticles, which can be considered coalesced nanoparticles. The microparticles may be produced using Method B:

Method B

In another exemplary embodiment of the present invention, hydrophobic silica microparticles are obtained using a method comprising the steps of;
  i) centrifuging a suspension of particles;
  ii) transferring the suspension of hydrophobic silica particles into an aqueous phase;
  iii) extracting the suspension from the aqueous phase into an organic phase;
  iv) evaporating the organic phase; and
  v) crushing and sieving the product obtained in step (iv).

According to exemplary embodiments, the suspension comprises a reaction product of a method corresponding to Method A disclosed herein. In an alternative exemplary embodiment, the hydrophobic silica microparticles are formed from silica nanoparticles that have been produced from methods other than Method A as disclosed herein.

The organic phase preferably comprises an organic solvent that is non-polar or has low polarity. In one exemplary embodiment, the organic phase is dichloromethane. In alternative exemplary embodiments, other organic solvents that can be used as an organic phase include, for example, alkanes, e.g., hexane, toluene, ethyl acetate, chloroform and diethyl ether.

Method C

In an alternative exemplary embodiment of the present invention, the hydrophobic silica microparticles are obtained from a reaction product produced from Method A by a method comprising the steps of:
  (a) centrifuging the reaction product; and
  (b) washing the reaction product in a fluid.

In one exemplary embodiment, the method comprises repeating steps (a) and (b) a plurality of times. Preferably, the fluid is an aqueous:solvent mixture and can be a water:organic solvent mixture. For example, the organic solvent can be ethanol. Preferably, the initial fluid comprises a mixture of water and organic solvent at a ratio of from about 60 (water): 40 (solvent) to about a 40:60 v/v mixture. In other exemplary embodiments, the solvent can be, for example, dimethylformamide, n-propanol or iso-propanol.

According to exemplary embodiments, the proportion of solvent in the mixture is increased between the initial washing (i.e., suspension) (step (b)) and the final washing (suspension). To obtain microparticles that are coalesced nanoparticles, the final suspension is dried. Preferably, the microparticles are then sieved. Once sieved, the microparticles are ready for application as a fingerprint developing agent.

The particles produced by carrying out Method B and/or Method C are microparticles, that is to say they have an average diameter in the order of micrometers, preferably from about 30 to about 90 μm. In some exemplary embodiments, the microparticles have an average diameter of from about 45 to about 65 μm or from about 65 to about 90 μm. The microparticles produced using Method B and/or Method C are considered to be coalesced nanoparticles.

Thus, disclosed herein is a method for making silica microparticles, e.g., having a diameter of at least 10 μm. The method can comprise the steps of:
  (i) a first step for making nanoparticles by a technique for controlling particle size, thereby enabling the formation of particles having an average particle size of about 500 nm+/−100 nm; and
  (ii) a second step for coalescing the nanoparticles into microparticles of a size suitable for removing by air filters (e.g., face masks) as in the case of microparticles having a diameter of at least about 5 μm, typically at least about 20 μm and preferably at least about 25 to 30 μm.

According to an exemplary embodiment, step (ii) can comprise drying the nanoparticles to encourage coalescing.

Method D

In an alternative exemplary embodiment of the present invention, hydrophobic silica nanoparticles are isolated from a reaction product produced from carrying out Method A. The hydrophobic silica nanoparticles are isolated using a method that comprises the steps of centrifuging the reaction product and suspending it in an aqueous:solvent mixture. In one exemplary embodiment, Method D is substantially similar to Method C, except Method D does not include the step of drying the nanoparticles.

In one exemplary embodiment, the aqueous:solvent mixture is a first aqueous:solvent mixture. The first aqueous:solvent mixture is preferably a 50:50 mixture.

In one exemplary embodiment, the method further comprises the steps of removing the reaction product from the first aqueous:solvent mixture, centrifuging it, and suspending it in a second aqueous:solvent mixture. Preferably, the second aqueous:solvent mixture has a substantially similar proportion of solvent and aqueous component as the first mixture.

In one exemplary embodiment, the aqueous solution that forms part of the aqueous:solvent mixture in Method C or Method D is water.

In an exemplary embodiment of the present invention, the solvent that makes up the solvent portion of the aqueous:solvent mixture is, for example, a water-miscible solvent. In one exemplary embodiment, the solvent is ethanol. In other exemplary embodiments, the solvent can be, for example, dimethylformamide, n-propanol or iso-propanol.

In one exemplary embodiment, the step of suspending the reaction product in an aqueous:solvent mixture and centrifuging it is repeated a plurality of times. Preferably, the composition of the aqueous:solvent mixture is altered to increase the proportion of solvent in the aqueous:solvent mixture over the course of repeated suspensions. Preferably, the method comprises, in the final step, suspending the reaction product in an aqueous:solvent "mixture" which is about 0% aqueous and about 100% solvent. The total number of suspensions can be from about 3 to about 10, for example, 4, 5, 6, 7, 8 or 9. For example, after each suspension, except the final suspension, the suspensions can be centrifuged. The nanoparticles can be stored in the final ethanolic suspension. It will be appreciated by those of ordinary skill that centrifugation is one exemplary method of isolating the nanoparticles from the aqueous:solvent mixture and other suitable separation techniques can be used.

The method of the present invention thus provides a suspension of hydrophobic silica nanoparticles in a solvent. The suspension can comprise trace amounts of the aqueous solution that forms part of the aqueous:solvent mixture.

The hydrophobic silica nanoparticles isolated using Method D are substantially spherical. The isolated nanoparticles preferably, although not essentially, have an average diameter from about 400 to about 500 nm. It is envisaged that nanoparticles of greater or lesser diameter, for example, from about 200 nm to about 900 nm or other any suitable diameter or range of diameters, can be produced by the present method. However, it is envisaged that the above method can produce nanoparticles that have an average diameter that is from about 200 nm to about 900 nm, for example, 200, 250, 300, 350, 400, 450, 500, 550, 600, 650, 700, 750, 800, 850 or 900 nm and any combination of sizes to form end-points of ranges. Each of the aforementioned diameter sizes can be combined with any other of the listed sizes to form end points of a size range of a particular exemplary embodiment. Thus, these are included exemplary embodiments in which the nanoparticles have an average diameter of from about 200 nm to about 300 nm, from about 400 nm to about 850 nm, or from about 300 nm to about 700 nm.

The term "average diameter" can be taken to mean a "mean diameter" of particles formed from the exemplary methods of the present invention. The term "mean" is a statistical term that is essentially the sum of all the diameters measured divided by the number of particles used in such measurements. The diameters of nanoparticles have been estimated from SEM pictures and the scale used in the picture, and for microparticles a combination of the sieve size, the results from particle size distribution measurements and from SEM pictures. One method that a mean diameter can be determined is by using an apparatus called the Malvern MASTERSIZER™ (manufactured by Malvern Instruments Ltd.).

Hydrophobic silica nanoparticles isolated using Method D can be in the form of a suspension in a water-miscible solvent.

Particles

In one aspect of the present invention, there are provided hydrophobic silica microparticles obtainable (having the characteristics of microparticles obtained) using Method B, Method C, Methods A and B combined or Methods A and C combined. The hydrophobic silica microparticles can comprise trace impurities such as, for example, trace amounts of the hydrolyzing agent, e.g., alkali, used in the method. Included, therefore, are silica particles comprising minor amount of component species of the alkali or hydrolyzing agent, e.g., ammonium, sodium or potassium. The microparticles can be considered to be aggregates of smaller silica nanoparticles.

In one exemplary embodiment, the microparticles produced using Method B, Method C, Methods A and B combined or Methods A and C combined can be used as a dusting agent for fingerprints and the like. In such an exemplary embodiment, the microparticles are of sufficient size to be efficiently captured using face masks and hence not inhaled. Thus, in one exemplary embodiment, the silica microparticles have an average diameter of at least about 10 μm, typically at least about 20 μm. According to an exemplary embodiment, the microparticles can have an average diameter of from about 30-90 μm. In some exemplary embodiments, the microparticles can have an average diameter of between about 45-65 μm or from about 65 to 90 μm.

In a further aspect of the invention, there is provided a dusting agent for use in fingerprint detection and/or analysis comprising hydrophobic silica microparticles. Alternatively, the microparticles can be suspended in an ethanolic aqueous mixture. However, the preferred form of an agent comprising microparticles is a dry particulate form, since the microparticles tend to sink in a suspension.

In one aspect of the invention, there is provided a suspension of hydrophobic silica nanoparticles in a solvent obtainable by Method D. In one exemplary embodiment, the solvent comprises ethanol. In other exemplary embodiments, the solvent can be another water-miscible solvent, e.g., one exemplified herein. In another exemplary embodiment, the suspension comprises a trace amount of the aqueous component of the aqueous:solvent mixture used in the method.

The physical nature and dimensions of the particles can be determined using SEM and TEM scans or the like. The particles are in the form of amorphous silica that can be used as an anti-caking agent in a variety of food products, and as an anti-caking agent and as an excipient in pharmaceuticals for various drug and vitamin preparations, as described in, for example, Expert Group on Vitamins and Minerals Secretariat, "Review of Silican," August 2002.

The nanoparticles formed from the methods according to exemplary embodiments of the present invention can be applied in a suitable liquid medium to latent fingerprints or to a surface to determine whether a fingerprint is present. For example, the suspension of nanoparticles in solvent produced by the method for isolating silica nanoparticles can be diluted with an aqueous component before use as a fingerprint detecting agent. The article in which a print is deposited can be immersed in the liquid medium (i.e., suspension of nanoparticles) and then removed. The length of immersion is not critical and can vary from about 15 minutes to about 12 hours or longer.

Thus, in a preferred exemplary embodiment, the nanoparticles are applied to a fingerprint or surface in a suitable liquid medium. The liquid medium can be an aqueous:solvent mixture. Therefore, in one aspect of the present invention, there is provided a suspension comprising hydrophobic silica nanoparticles, an aqueous component and a water-miscible solvent. In one exemplary embodiment, the aqueous component comprises water. The solvent can be, for example, a water miscible solvent, e.g., substantially 100% miscible in all proportions in water. In one exemplary embodiment, the solvent comprises ethanol. The water:solvent ratio ranges from about 99.9:0.1 (water:solvent) to about 96:4 (water:solvent). The level of solvent preferably is not greater than about 4%, since a higher level of solvent may result in the fingerprints becoming dissolved or their definition reduced. It is preferable to include at least a trace amount of solvent to ensure that the nanoparticles remain as discrete particles and do not coalesce to form aggregates.

It will be understood by skilled artisans that the term "fingerprint" includes reference to a partial print and/or to prints of other body parts, and that, for example, the silica particles can be applied to a portion of a fingerprint. Typically, a fingerprint is lifted from its underlying surface prior to analysis, and the term "fingerprint" accordingly includes lifted fingerprints. According to an exemplary embodiment, the fingerprint is lifted prior to application of the particles.

According to an exemplary embodiment, the hydrophobic silica nanoparticles should not form aerosols during the application process and therefore should be safe to apply. It should also be noted that the nanoparticles are too large to cross biological membranes such as skin and lung tissue. Hence, both forms, i.e., microparticles and nanoparticles, should be safe agents when used in the contexts described above.

The methods described above produce a range of stable silica micro- and nanoparticles. However, in order to be able to visualize these particles, it is advantageous to incorporate a variety of dyes within them.

Thus, in an exemplary embodiment of the present invention, the methods further comprise the step of incorporating a dye or other imaging agent into the silica particle. To achieve incorporation of small molecules such as dyes (e.g., colored or fluorescent), functional groups are incorporated within the particle, forming strong binding interactions with the dye molecules. These functional groups are either hydrophobic or hydrophilic, or combinations of both.

The functional groups are present in one or more of the silane ether monomers and it is presumed that, when the dye molecules are added, interactions are formed between the dye molecules and appropriate functional groups provided by the monomers to maximize the interactions between the two components of the mixture.

According to exemplary embodiments, it is believed that addition of the catalyst, for example, ammonium hydroxide, results in polymerization and the dye-backbone interactions are frozen resulting in pockets of folded backbone in which are located the dye molecules. The dye molecules cannot be easily extracted using aqueous solutions from the resulting particles and this may be due to the compact folding of the backbone around the dye molecules that results in pores that are smaller than the dye molecules themselves, or in substructures in which the binding interactions. One example of such binding interactions is hydrophobic interactions between the planar aromatic groups within the polymer of PTEOS derived particles and the dye molecule. Other examples are ionic interactions between positively charged groups on the dye molecules and the adjacent negatively charged groups, for example, Si—O groups on the polymer backbone are sufficiently large to retain the dyes within the matrix even in the presence of large diameter pores.

As described earlier, the ratio of silane ether monomers, for example, TEOS and organically substituted silane ether monomers, for example, PTEOS, is preferably about 1:1 v/v. It is at this ratio that the optimum incorporation and, therefore, retention of a dye molecule within the silica particle is demonstrated. However, it will be understood by the skilled artisan that other ratios can be used that will result in the incorporation and retention of the dye molecule, and, therefore, enable the detection of the particle.

In an exemplary embodiment, the dye to be incorporated into the particle can be, for example, a colored or a fluorescent dye or the like. Examples of dyes include, but are not limited to, fluorescein derivatives, for example, Oregon Green, Tokyo Green, SNAFL, and carboxynapthofluorescein, rhodamine (e.g., rhodamine B and rhodamine 6G) and analogues thereof, thiazole orange, oxazine perchlorate, methylene blue, basic yellow 40, basic red 28, and crystal violet, and analogs thereof. According to exemplary embodiments, it is considered that dyes that are positively charged, for example, rhodamine, are better incorporated when PTEOS is used in the method than dyes that comprise anionic or cationic group such as carboxylic groups. Examples of other dyes that could be used in the present invention include those that possess a planar aromatic substructure and positively charged functional groups (e.g., ethidium bromide and other DNA intercalating agents).

Preferably, the dyes are incorporated from aqueous solutions during the single-step reaction step described above (Method A), that is to say, the dye is included in the reaction mixture of TAOS (e.g., TMOS and/or TEOS) and PTEOS monomers.

It may be advantageous for the particles to be magnetic or paramagnetic. For example, magnetizable microparticles can easily be dusted over fingerprints, using a magnetic wand or other appropriate tool. In a preferred embodiment of the present invention, therefore, magnetic or paramagnetic subparticles can be incorporated into the monomer mixture in Method A. In an exemplary embodiment of the present invention, the particles of the invention are magnetizable, e.g., magnetic or paramagnetic.

In one exemplary embodiment, the methods for preparing hydrophobic silica particles further comprise including magnetic or paramagnetic particles in a reaction mixture of silane ether monomers, for example, TAOS (e.g. TEOS) monomers and organically modified silane ether monomers, for example, PTEOS monomers. Thus, preferably, the magnetic or paramagnetic particles can be incorporated during the single-step reaction step described above (Method A). The magnetic and/or paramagnetic particles can be any suitable magnetic or paramagnetic component, for example, metals, metal nitrides, metal oxides, carbon and the like. Examples of magnetic metals include, for example, iron, while examples of a metal oxide include, for example, magnetite. Carbon can be in the form of, for example, carbon black, fullerene or carbon nanotubes (derivatized or non-derivatized carbon nanotubes). The carbon nanotubes can be multi-walled carbon nanotubes and/or single walled carbon nanotubes.

Hydrophobic silica particles containing both a magnetizable material and also a separate imaging material (particularly a dye, e.g., a fluorescent or colored dye) are novel and form part of the present invention.

In one exemplary embodiment, the magnetizable material can be magnetic or paramagnetic particles comprising, for example, magnetite, that is included in the reaction mixture of silane ether monomers, for example TAOS (e.g., TEOS) monomers and organically modified silane ether monomers, for example, PTEOS monomers. "Pale brown" particles can be formed when haematite is included in the mixture. Black particles can be formed when magnetite is included in the mixture. Both types of incorporated particles are found to be highly magnetizable.

According to some exemplary embodiments, Method A comprises, for example, titanium dioxide or carbon black in the reaction mixture. Other examples of "white" or "grey" particles are formed when either titanium dioxide or Carbon Black particles respectively are included in the reaction mixture of (1) silane ether monomers, for example TAOS (e.g., TEOS) monomers, and (2) organically modified silane ether monomers, for example, PTEOS monomers, mixture during synthesis. The relatively large size of these particles results in their entrapment within the polymer matrix while producing the required hydrophobic silica particles. The color of the "grey" particles is dependent on the amount of carbon black or titanium dioxide included in the TAOS (e.g., TEOS)/PTEOS mixture during synthesis. A higher level of carbon black or titanium dioxide results in a darker particle.

As an alternative, or in addition, to the particles comprising a magnetizable element, the hydrophobic silica particles can be mixed with a magnetic substance, for example, iron filings or the like, to form a magnetizable agent that can be applied to fingerprints.

Conventional methods of fingerprint detection include the step of applying a magnetic substance, including, for example, using iron particles that are coated with a hydrophobic substance such as stearic acid. Such a form of fingerprint detection often has the disadvantage that the iron particles can be rubbed off onto a fingerprint, thus causing depletion of the iron and reducing the amount available for future administration. One advantage of incorporating magnetic particles into the silica particles during synthesis is that the level of magnetic substance to be applied remains constant since the amount of magnetic particle per silica particle tends not alter significantly.

In a further exemplary embodiment of the present invention, the method for preparing hydrophobic silica particles, using a hydrolyzing agent, e.g., an alkali, comprises the step of mixing magnetic micro- or nanoparticles with iron filings to generate a range of magnetizable particles.

According to a further aspect of the present invention, there is provided a hydrophobic silica particle obtainable by the methods of the present invention or that has the characteristics of a particle made by the methods of the present invention. In one exemplary embodiment, there is provided a hydrophobic silica microparticle.

In one exemplary embodiment, the invention provides a hydrophobic silica nanoparticle having a diameter of between about 200 to about 900 nm, preferably about 300 to about 600 nm, and more preferably about 400 nm to about 500 nm.

In one exemplary embodiment, the hydrophobic silica particle (microparticle and/or nanoparticle) comprises a dye. Examples of such dyes are described above in the present specification. The dye may be colored or fluorescent and can provide visualization means that enable the particles to be seen.

In an exemplary embodiment, the silica particle further comprises a magnetizable element, for example, a magnetizable particle. In one embodiment, the particle comprises magnetite and/or haematite.

In an exemplary embodiment, the silica particle comprises a dye and a magnetizable element.

In an exemplary embodiment, the silica particle comprises a metal, metal oxide, metal nitride and/or a carbon molecule, e.g., carbon black and/or titanium dioxide, either alone or in combination with a dye and/or magnetizable element, for example magnetite.

The hydrophobic silica particles of the present invention can be used in the process of fingerprint detection and identification. Thus, in one aspect of the present invention, there is provided use of a hydrophobic silica particle as described herein, for example, a silica particle obtainable by the methods of the present invention, in the detection and/or identification of a fingerprint. In an exemplary embodiment, hydrophobic silica particles that have the characteristics of a particle are obtained by one or more of the methods of the present invention.

In one exemplary embodiment, the use comprises imaging a fingerprint.

In one exemplary embodiment, there is provided the use of the hydrophobic silica micro- and nanoparticles according to the invention for fingerprinting. In one exemplary embodiment, the silica particles of the present invention are used as agents for dusting and/or developing a fingerprint.

Thus, in one aspect of the present invention, there is provided an agent for dusting a fingerprint comprising hydrophobic silica particles. In one exemplary embodiment, the particle is a microparticle. In an alternative exemplary embodiment, the agent includes hydrophobic silica nanoparticles. In one exemplary embodiment, the agent for dusting comprises hydrophobic silica particles that comprise a dye molecule. In one exemplary embodiment, the dusting agent comprises hydrophobic silica particles that comprise a magnetizable element. Thus, the silica particles can be magnetic or paramagnetic. In one exemplary embodiment, the dusting agent comprises hydrophobic silica particles that comprise both a magnetizable element and a dye molecule. In an alternative exemplary embodiment, the agent comprises a mixture of hydrophobic silica particles and a magnetizable material, for example, iron filings or the like.

A latent fingerprint, deposited by the fingertip pattern, is a complex mixture of natural secretions and contaminations from the environment. The latent prints can be fresh or aged finger prints. The residues within aged prints mainly consist of hydrophobic endogenous chemicals secreted by the donor. Thus, the dusting agent of the present invention can be used to detect and/or identify both fresh and aged fingerprints.

In a further aspect of the present invention, there are provided hydrophobic silica microparticles comprising aggregates of nanoparticles. The microparticles of the present invention can be used as dusting agents, e.g., in the form of a powder, for latent prints on a variety of porous and semiporous surfaces. The microparticles can be applied using standard commercial brushes or via a commercial magnetic wand for magnetic particles. If the microparticles incorporate magnetic subparticles and/or have been mixed with iron filings (e.g., to generate a range of magnetizable particles) then these particles can be applied to the prints using a magnetic wand. The microparticles can additionally comprise a dye and/or colored particle.

In an exemplary embodiment, the silica microparticles or nanoparticles can be applied directly to the surface as a suspension. Thus, in one aspect of the present invention, there is provided a suspension for detecting fingerprints comprising silica particles of the present invention. In one exemplary embodiment, the suspension comprises water and ethanol. This is particularly advantageous as it allows objects, e.g., weapons, to be submerged in the suspension, thus increasing the likelihood of detecting a latent print on any surface of the object.

According to a further aspect of the present invention, there is provided the use of a hydrophobic silica particle as an agent for developing a deposit, e.g., latent fingerprints, on a surface. The use can further comprise imaging the fingerprint.

In one aspect of the present invention, there is provided a method of detecting and/or identifying fingerprints comprising the step of contacting a fingerprint with an agent comprising the silica particles of the present invention.

According to exemplary embodiments, the method further comprises the steps of visualizing and/or imaging the fingerprint.

In one exemplary embodiment, the agent is a dusting agent. In an alternative exemplary embodiment, the agent is a suspension as described herein. When the agent is a suspension, the method can further comprise the step of drying the fingerprint prior to visualizing the fingerprint.

The step of visualizing the fingerprints can be carried out using various methods known to those of skill in the art. For example, optical methods can be used, for example, a UV search light, optical scanner including a flat-bed optical scanner, a fluorescent scanner and a UV visible scanner, or other suitable visualizing means.

MATERIALS AND METHODS
Materials

Ethanol (99.7%) was purchased from Hayman Ltd., UK. Tetraethoxysilane (98%+), crystal violet, thiazole orange, oxazine 1 perchlorate and titanium dioxide were purchased from Aldrich, Dorset, UK. Phenyltriethoxysilane was supplied by Fluorochem, Derbyshire UK. Bromothymol blue and methylene blue were purchased from BDH Chemicals Ltd, now VWR International Ltd., Leicestershire, UK. Ammonium hydroxide solution (28%), sodium fluorescein, Rhodamine B and Rhodamine 6G were purchased from Sigma-Aldrich, Dorset, UK. The carbon black solution was obtained from Cabot Corp., Cheshire, UK. The nanoparticulate magnetite was synthesized in-house according to previously published methods, such as those described in, for example: J. J. Harbum, R. R. Ritter, C. D. Spilling, K. M. Miller, "Magnetically Responsive Particles and Embolic Materials using Coated Magnetically Responsive Particles," U.S. patent application Ser. No. 10/623,863, filed Jul. 21, 2003; and L. A. Harris, J. D. Goff, A. Y. Carmichael, J. S. Riffle, "Magnetite Nanoparticle Dispersions Stabilized by Triblock Copolymers," Chemistry of Materials, 15 (2003) page 1367, the entire contents of each of which are hereby incorporated by reference herein.

Preparation of TEOS:PTEOS-Derived Particles

For purposes of illustration and not limitation, the method for the preparation of blank micro- or nanoparticles includes mixing 30 ml ethanol, 5 ml dH$_2$O, 2.5 ml of tetraethoxysilane (TEOS) and 2.5 ml phenyltriethoxysilane (PTEOS) in a centrifuge tube. To this mixture, add 2 ml ammonium hydroxide solution and rotate the solution overnight. After this time, centrifuge the suspension (e.g., 3 minutes at 3,000 rpm).

Method 1

The present method yields microparticles. The method includes the centrifugation and liquid/liquid phase extraction into dichloromethane from water, followed by evaporation of the organic phase to dryness, yielding a glass-like sheet of coalesced particles. The sheet of coalesced particles is crushed using a mortar and pestle and the resulting particles sieved through brass test sieves with bronze mesh (such as those that can be obtained from Endecot Ltd., London UK) by hand.

The particle size fractions used in the present method are about 38-45, 45-63 and 63-90 and these were each used as dusting agents. A Malvern MASTERSIZER™ (Malvern Instruments Ltd., Malvern, UK) can be used to verify the particle size distributions. Due to the hydrophobicity of the particles, ethanol can be used as the solvent. A Hitachi Scanning Electron Microscope (SEM) can be used to visualize the particles and a Hitachi Transmission Electron Microscope (TEM) can be used for electron diffraction patterns.

Method 2

The present method yields nanoparticles. The product is isolated following a series of centrifugation and washing steps using about 10:90 v/v ethanol/water and then retained as a suspension in about 97:3 v/v water/ethanol. These were also subjected to particle size distribution analysis and SEM and TEM.

Method 3

The present method yields nanoparticles. The product is isolated following two washes with a 50:50 mixture of water:ethanol, followed by a wash using 25:75 mixture of water:ethanol and a final wash using 0:100 mixture of water:ethanol. The reaction product was then resuspended in as little ethanol as possible to transfer to a drying dish. The suspension was left at room temperature for several days before being kept at a temperature of about 37° C. for several days.

For the different dye doped particles, the relevant dye (e.g., 25 mg) is dissolved into the ethanol prior to the addition of the other silanization reagents. The titanium dioxide embedded particles are prepared by adding approximately 25 mg of titanium dioxide to the centrifuge tube, prior to the addition of the silanization reagents. For carbon black particles, about 5 ml of a 1:100 fold dilution of the carbon black suspension in water is added to the precursor solution. For TEOS:PTEOS coated magnetic particles, particulate magnetite is prepared according to published methods and 5 ml of the suspension in water is included in the precursor solution.

Figure 2A:
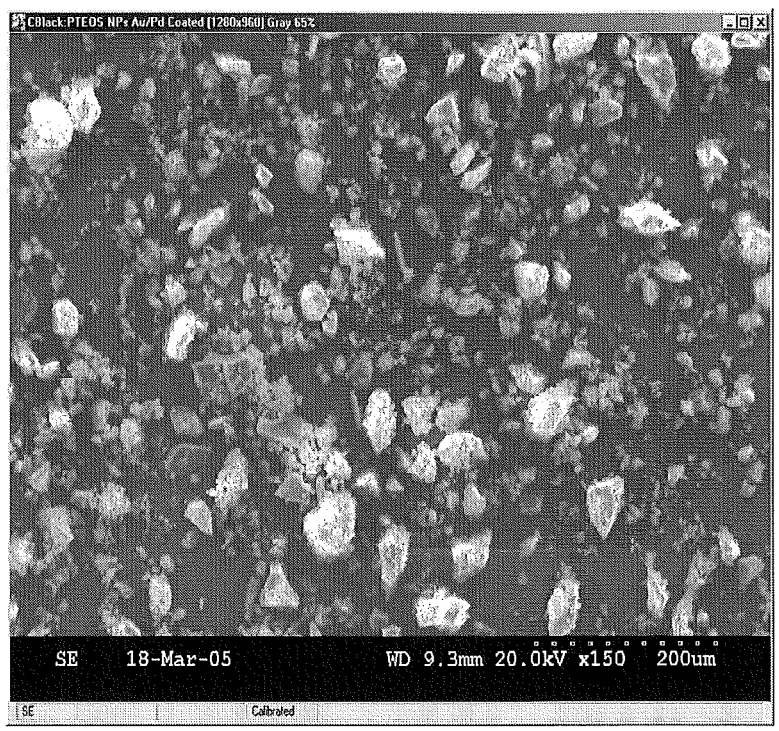
FIGS. 2A and 2B are pictures taken by a scanning electron microscope of carbon black embedded microparticles, in accordance with an exemplary embodiment of the present invention.
Figure 2B:
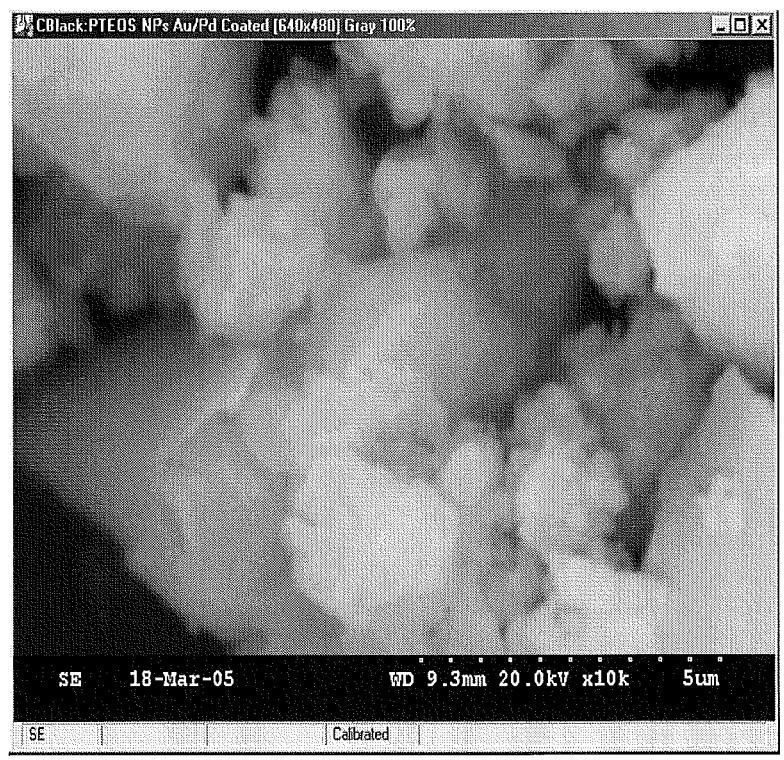
Figure 3:
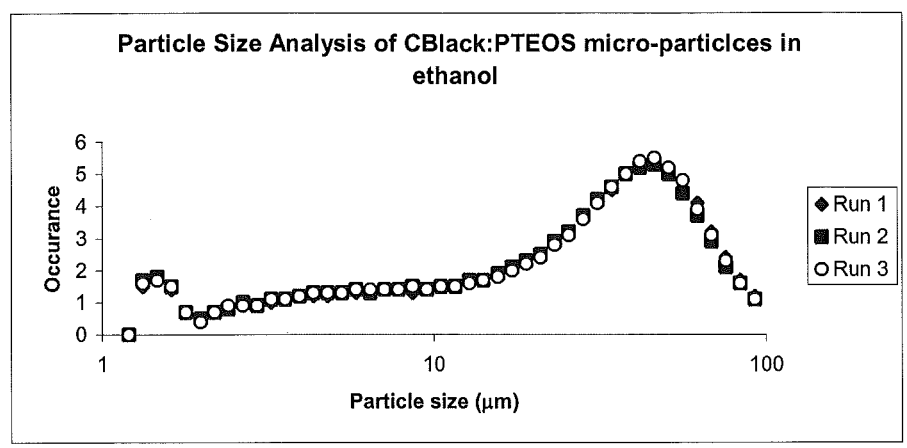
FIG. 3 is a graph illustrating size distribution for hydrophobic microparticles with embedded carbon black obtained through a 38-63 µm mesh, in accordance with an exemplary embodiment of the present invention.

Using the two methods described above, a range of microparticles and nanoparticles were produced. SEMs are illustrated for carbon black-embedded nanoparticles in FIG. 1, and for carbon black-embedded microparticles in FIGS. 2A and 2B. The nanoparticles are comprised of discrete spherical particles with an average diameter of about 400-500 nm, whereas the microparticles are comprised of aggregates of nanoparticles with an average diameter of about 27 μm for the 38-63 μm-sieved fraction, as illustrated in graph 300 of FIG. 3.

Figure 4A:
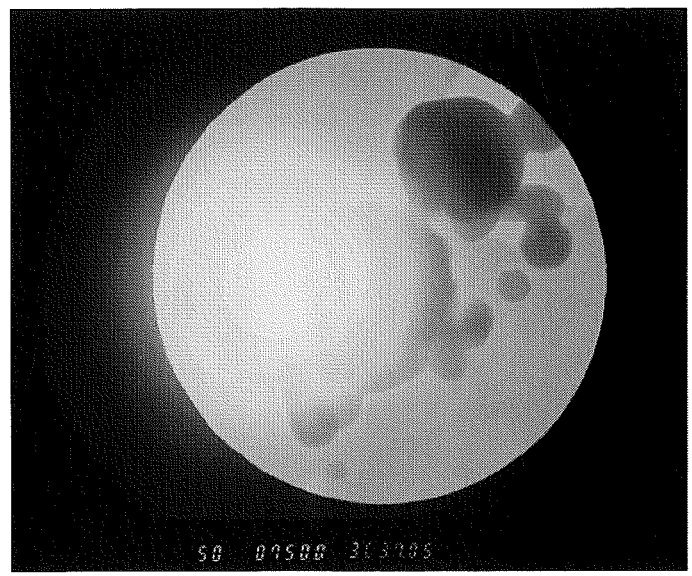
FIG. 4A is picture illustrating electron diffraction patterns for amorphous silica nanoparticles, in accordance with an exemplary embodiment of the present invention.
Figure 4B:
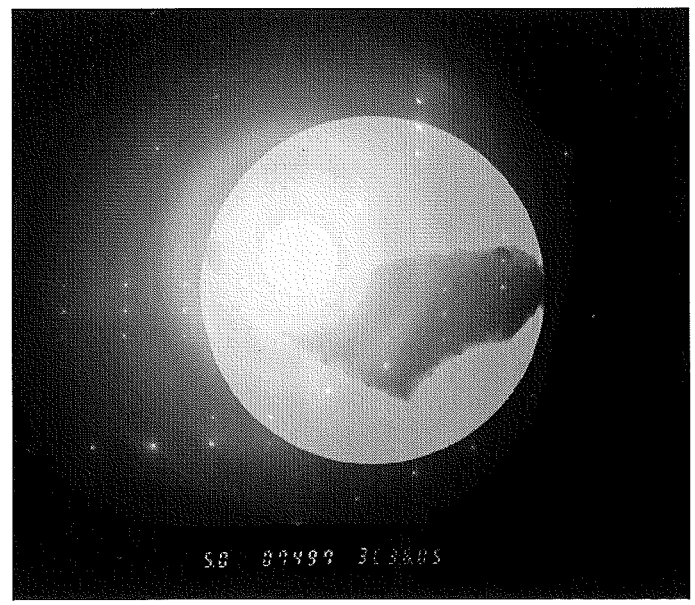
FIG. 4B is a picture illustrating electron diffraction patterns for α-quartz, in accordance with an exemplary embodiment of the present invention.

The TEM data (illustrated in FIG. 4A) show no regular diffraction pattern for the silica nanoparticles, demonstrating that that the particles are comprised of amorphous, non-crystalline silica. This is in contrast to the diffraction pattern observed with crystalline silica (illustrated in FIG. 4B).

A variety of fluorescent and colored hydrophobic particles were prepared according to exemplary embodiments. In addition, a variety of white, grey and magnetic sub-particles were also incorporated within the hydrophobic silica microparticles. The relatively large size of these particles resulted in their entrapment within the polymer matrix while producing the required hydrophobic silica particles. White particles were formed when titanium dioxide was included in the TEOS/PTEOS mixture, grey particles when carbon black was included, and pale brown when haematite was included, or black when magnetite was included. The magnetite-incorporated and haematite-incorporated particles were found to be highly magnetizable.

EXAMPLE 1

The Effect of TEOS:PTEOS Ratios on Incorporation of Ethidium Bromide and Dyes

The present example was performed using the method as detailed above, with ratios of TEOS:PTEOS varying from about 1:0, 0.9:0.1, 0.8:0.2 and 0.7:0.3. Ethidium bromide, crystal violet, bromothymol blue and analogs of rhodamine were used to test the mechanism for effective dye incorporation.

(i) Ethidium Bromide (EtBr)

Figure 5:
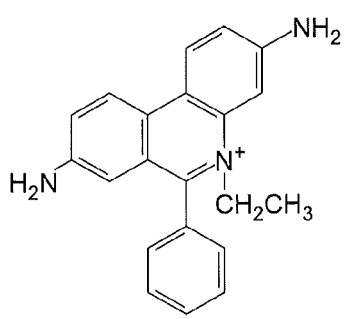
FIGS. 5A-5E are block diagrams illustrating structures of colored and fluorescent dyes, in accordance with an exemplary embodiment of the present invention.
Figure 5:
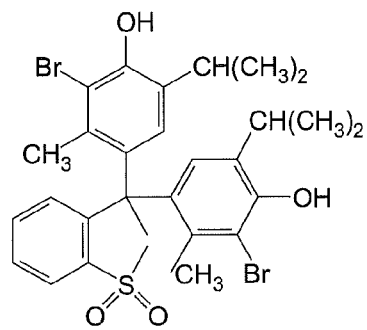
Figure 5:
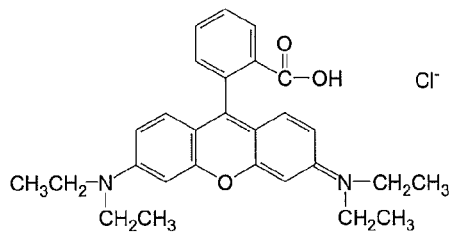
Figure 5:
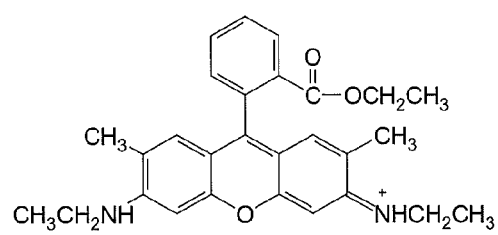
Figure 5:
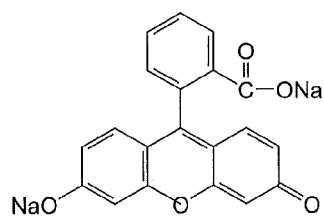
Figure 5:
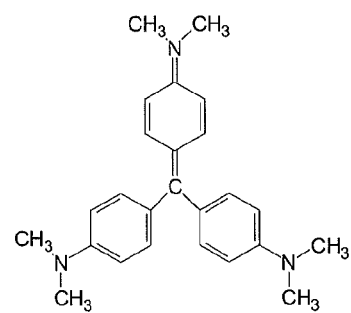

Ethidium Bromide (FIG. 5A) is used extensively as a fluorescent marker for DNA with which it forms a highly fluorescent complex due to its intercalation between base pairs of the DNA a-helix. Such intercalation results from a combination of strong hydrophobic bonds between the planar base pairs within the interior of the DNA chains and the planar aromatic rings of the dye, and electrostatic bonds between the negatively charged phosphate groups of DNA and the positively charged group of the dye. The planar aromatic phenyl groups of PTEOS form hydrophobic interactions with the planar rings of EtBr and the negatively charged Si—O groups present in PTEOS and TEOS form electrostatic bonds with the positively charged nitrogen of EtBr, thus simulating the intercalation seen with DNA, and thus producing a highly fluorescent and stable complex on polymerization when nanoparticles are formed. Nanoparticles formed with TEOS and EtBr were of low fluorescence, since the dye was washed from the particles following their formation. In contrast, when PTEOS was added, highly fluorescent particles were formed that retained the dye on washing. It was also noted that the intensity of the dye's fluorescence increased as the proportion of PTEOS in the initial monomer mixture increased. A ratio of 1:1 v/v was used thereafter in all incorporation experiments. However, it was found that this dye is prone to photo-bleaching under exposure to high intensity UV illumination, and, hence, was not a suitable reporter system for fingerprint development work.

(ii) Crystal Violet {CV} and Bromothymol Blue (BTB).

Crystal violet (CV) and bromothymol blue (BTB) (illustrated in FIGS. 5F and 5B, respectively), were independently included in a mixture 1:1 mixture of PTEOS and TEOS monomers. Both dye molecules are similar to EtBr, in that they include planar phenyl groups, but CV contains a quaternary ammonium group and secondary amino groups similar to those present in EtBr, whereas BTB is an acidic molecule having phenolic and sulphonic acid groups. CV-incorporated nanoparticles produced particles with a dark purple color. Such as result may be due to the amino groups in CV producing strong attractive interactions with the silane residues. In comparison, the BTB particles were off-white, as the BTB dye was not found to be retained within the silica nanoparticles on workup, possibly due to repulsion between the negatively ionized acidic groups of BTB and the negatively charged Si—O groups within the monomers.

(iii) Analogs of Rhodamine

Rhodamine B (illustrated in FIG. 5C) yielded a dark red powder whilst rhodamine 6B (not shown) yielded an orange powder, both of which were intensely fluorescent.

EXAMPLE 2

The Effect of APTES on Incorporation of Dyes into TEOS/PTEOS Sol Gels

The present example was performed using the above method for the preparation of TEOS:PTEOS particles. In addition, the same dyes were used, but APTES was incorporated into the monomer mixture. Here, a ratio of about 3:3:6 of PTEOS:APTES:TEOS was used (about 1.25 ml:1.25 ml:2.5 ml) instead of the usual (about 2.5 ml:2.5 ml) PTEOS:TEOS ratio. The dyes used were fluorescein, thiazole orange, oxazine perchlorate, methylene blue, basic yellow 40 and basic red 28. In addition, two types of rhodamine were used, rhodamine B and rhodamine 6G. In each case, the dye-doped particles were isolated as ground and sieved microparticles.

A wide variety of stable dye-doped particles were formed. In each case, the dyes were incorporated into microparticles from aqueous solutions, using the PTEOS and TEOS method. For example Rhodamine B yielded a dark red powder, while rhodamine 6B yielded an orange one. Both were intensely fluorescent. In contrast, when APTES was included in the mixture of monomers, the resulting powder was pale pink and of low residual fluorescence. The same phenomenon was observed for sodium fluorescein, when addition of APTES again resulted in poor incorporation of the fluorescent dye and producing a barely fluorescent off white powder. These results indicate that the presence of the amino groups in the silica particles destabilizes dye-polymer interactions producing particles from which the dyes can be extracted under aqueous work-up conditions.

EXAMPLE 3

The Use of Dye-Doped Hydrophobic Nanoparticle Suspensions as Developing Agents for Latent Fingerprints Both fresh (approximately 20 minutes prior to dusting) and aged prints (various conditions detailed within) were studied. The fingerprints were deposited by a 21 year old Caucasian female and a 33 year old Caucasian male onto non-porous glass microscope slides (such as those that can be obtained from VWR Int.). Two methods were used for development. A small volume of suspension (500 µl of a 10% w/v in 97:3 v/v water/ethanol) was applied to the print using a dropping pipette. After about 2-3 minutes, the excess suspension was removed by gently washing with excess water. The print was then left to air dry. Alternatively, the slide was immersed in the suspension for about 2-3 minutes. The excess developer was removed by gravity and the surface allowed to air dry as before.

The resulting fingerprints were visualized by different optical methods. For the fluorescent observations, a hand held UV search light (λ415 nm) from CSI Ltd. was used. For further fluorescent imaging and capture, a Tecan LS300 optical scanner (Tecan UK, Theale, UK) was used. The developed fingerprints were also digitally captured using a Nikon Coolpix 5400 camera.

Figure 6:
FIGS. 6A-6D are prints developed with rhodamine 6G-incorporated particles, applied as a nanoparticle suspension (FIGS. 6A and 6B) and as a dusting powder (FIGS. 6C and 6D), with white light illumination used for FIGS. 6A and 6C and UV illumination used for FIGS. 6B and 6D, in accordance with an exemplary embodiment of the present invention.
Figure 6:
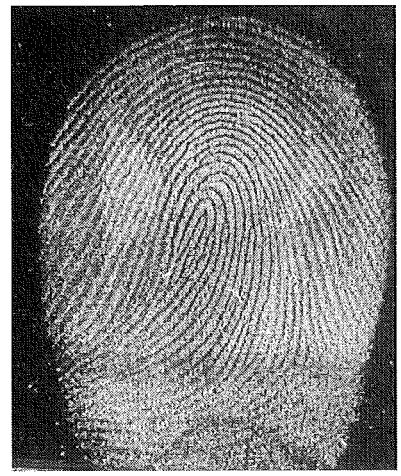
Figure 6:
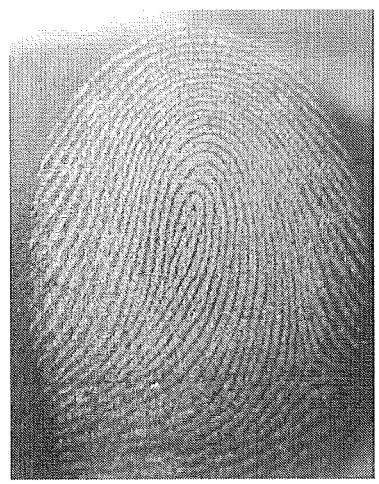
Figure 6:
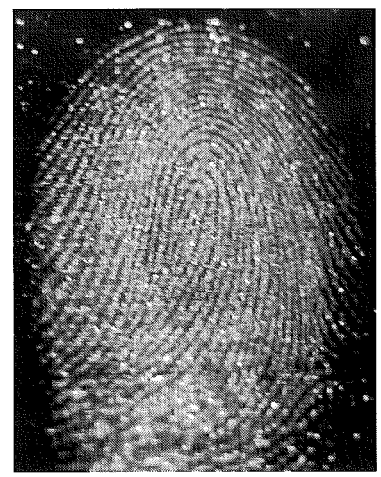

Both fluorescent and colored nanoparticles were successfully used as developing agents for both fresh and aged prints. Examples of the former are illustrated in FIGS. 6A and 6B for particles with incorporated rhodamine 6G, and of the latter in FIG. 7B for particles with crystal violet-incorporated dye. Excellent definition was seen in both cases under white light illumination and under UV illumination for the fluorescent particles (see FIG. 6B).

Figure 8:
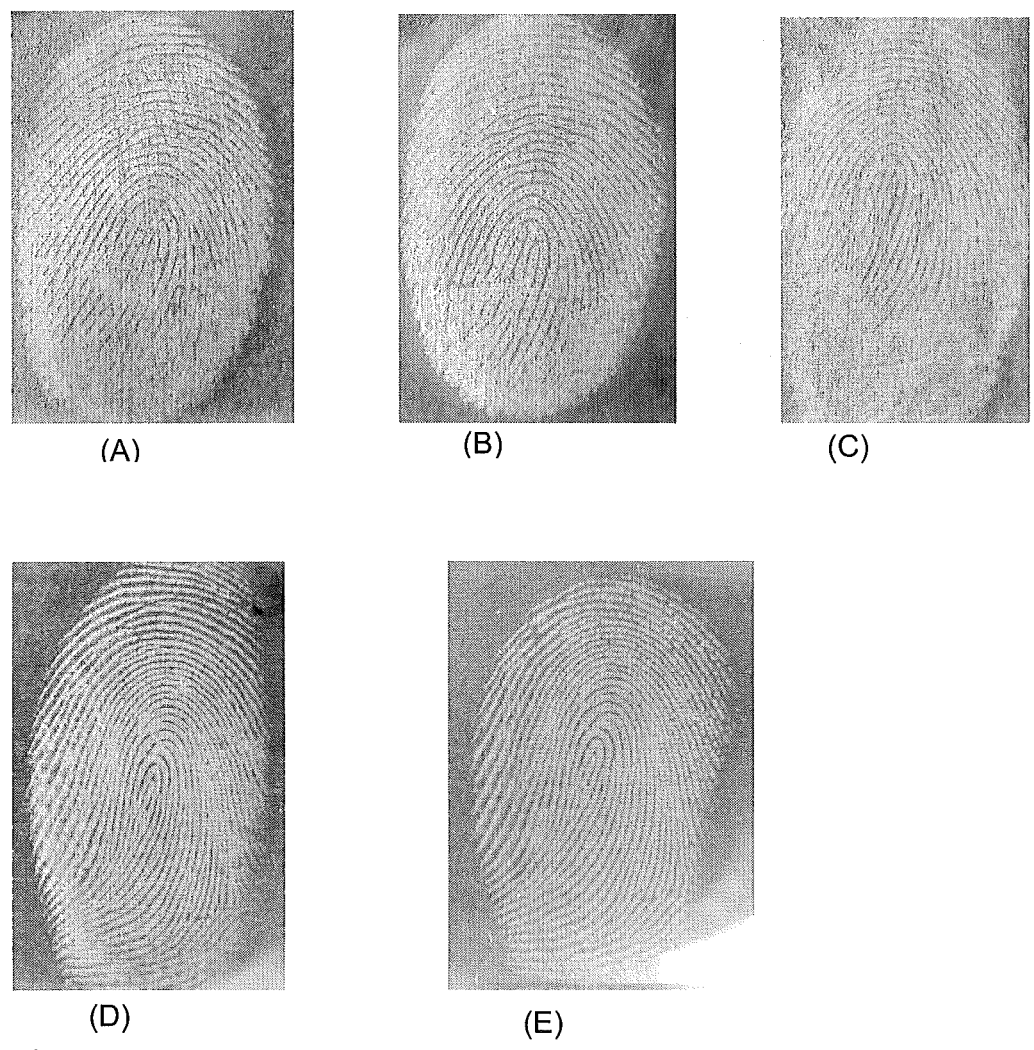
FIGS. 8A-8E are pictures illustrating examples of dusted aged prints on glass, with incorporated sub-particles (FIGS. 8A-8C) or dyes (FIGS. 8D-8E)

FIGS. 8A-8E illustrate examples of prints obtained by conventional dusting with microparticles incorporating carbon black (FIG. 8A), titanium dioxide (FIG. 8B), magnetite (FIG. 8C), crystal violet (FIG. 8D), and methylene blue (FIG. 8E). Excellent definition was observed with all the particles demonstrating the universality of the approach. However, for dusting, particles of diameter of approximately 45-63 µm gave the best results.

EXAMPLE 4

The Use of Dye-Doped Hydrophobic Microparticles as Dusting Agents for Latent Fingerprints The dye-doped particulate powders developed according to exemplary embodiments were brushed onto the latent fingerprints using either a squirrel hair brush or a glass fiber (Zephyr) brush. The carbon black and titanium dioxide containing particles were applied using a glass fiber (Zephyr) brush. The in-house developed magnetic powders were applied with commercial plastic magnetic brushes (such as those that can be obtained from Crime Scene Investigation Equipment Ltd., Northampton, UK).

The resulting fingerprints were visualized by different optical methods. For the fluorescent observations, a hand held UV search light ($\lambda$ 415 nm) from CSI Ltd. was used. For further fluorescent imaging and capture, a Tecan LS300 optical scanner (Tecan UK, Theale, UK) was used. The developed fingerprints were also digitally captured using a Nikon Coolpix 5400 camera.

Figure 7:
FIGS. 7A and 7B are pictures illustrating detail of 40-day old print dusted with crystal violet-incorporated microparticles (FIG. 7A) and a print from the same donor developed with a suspension of crystal violet-incorporated nanoparticles (FIG. 7B), in accordance with an exemplary embodiment of the present invention.
Figure 7:

A variety of fractions from sieving were used as dusting agents. The one which gave greatest ease of application and produced prints of best definition were those with from sieve size of approximately 45-63 µm for fluorescent and colored particles and approximately 63-90 µm for the sub-particle embedded particles. Examples of prints developed with fluorescent dye (rhodamine 6G) is illustrated in FIGS. 6C and 6D, under white (FIG. 6C) and UV (FIG. 6D) illumination. FIGS. 7A and 7B illustrates a dusted print from a 40 day old sample on glass produced by applying crystal violet-incorporated dye (FIG. 7A). Generally, better definition was observed with the fluorescent and dye-doped particles (FIGS. 8A-8E), but the embedded particles still produced prints with good definition.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the present invention are to be understood to be applicable to any other aspect, embodiment or example described herein unless incompatible therewith.

Throughout the present disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range, such as from 1 to 6, should be considered to have specifically disclosed sub-ranges, such as from 1 to 3, from 1 to 4, from 1 to 5, from 2 to 4, from 2 to 6, from 3 to 6 and the like, as well as individual numbers within that range, for example, 1, 2, 3, 4, 5, and 6. This applies regardless of the breadth of the range. It should also be understood that description of a number of ranges should be considered to have specifically disclosed a combination of end points.

It will be appreciated by those of ordinary skill in the art that the present invention can be embodied in various specific forms without departing from the spirit or essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

All United States patents and applications, foreign patents and applications, and publications discussed above are hereby incorporated by reference herein in their entireties.

What is claimed is:

1. A method for detecting a hydrophobic mass, comprising:
    contacting an area comprising a hydrophobic mass with an agent comprising hydrophobic silica particles, wherein the silica particles comprise a dye and/or colored particles; and
    detecting, based upon the step of contacting an area, that the area contains the hydrophobic mass, the hydrophobic mass comprising a hydrophobic deposit,
    wherein the silica particles are obtained by a method comprising reacting together in a single step a mixture of silane ether monomers and organically modified silane ether monomers with a hydrolyzing agent.

2. The method according to claim 1, which comprises applying the agent as a dusting agent or as a suspension to the area.

3. The method according to claim 1, wherein the silica particles are obtained by a method in which the silane ether monomers are TAOS (tetraalkoxysilane) monomers.

4. The method according to claim 1, wherein the silica particles are obtained by a method in which the organically modified silane ether monomer comprises an aryl containing group.

5. The method according to claim 1, wherein the silica particles are obtained by a method which comprises reacting together in a single step a mixture of TEOS (tetraethoxysilane) and PTEOS monomers (phenyltriethoxysilane) with the hydrolysing agent.

6. The method according to claim 5, wherein the silica particles are obtained by a method in which the hydrolysing agent is an acid or an alkali.

7. The method according to claim 6, wherein the silica particles are obtained by a method in which the alkali is a hydroxide.

8. The method according to claim 7, wherein the alkali is ammonium hydroxide.

9. The method according to claim 1, wherein the silica particles are obtained by a method in which the dye molecules and/or colored particles are included in the mixture of the monomers and the hydrolysing agent and are thereby incorporated into the hydrophobic silica particles.

10. The method according to claim 1, further comprising visualizing or imaging the hydrophobic mass, wherein the silica particles comprise a visualization or imaging agent and the method comprises visualizing and/or imaging the silica particles after the surface has been contacted with them.

11. The method according to claim 10, wherein the silica particles comprise a dye molecule for imaging the hydrophobic mass.

12. The method according to claim 1, further comprising visualizing the hydrophobic mass using an optical method, optionally wherein the optical method is selected from the group consisting of a UV search light, an optical scanner including a flat-bed optical scanner, a fluorescent scanner and a UV visible scanner.

13. The method according to claim 1, wherein the silica particles comprise a magnetic or paramagnetic particle that allows the agent to be applied to the area using a magnetic applicator.

14. The method according to claim 1, wherein the silica particles are microparticles having an average diameter of from about 10 to about 90 µm, optionally from about 45 to about 65 µm and further optionally from about 65 to about 90 µm.

15. A method for detecting a hydrophobic mass, comprising:
- contacting an area comprising a hydrophobic with an agent comprising hydrophobic silica particles, wherein the silica particles comprise a dye molecule for imaging the hydrophobic mass and/or colored particles;
- detecting, based upon the step of contacting an area, that the area contains the hydrophobic mass, the hydrophobic mass comprising a hydrophobic deposit; and
- visualizing or imaging the hydrophobic mass, wherein the silica particles comprise a visualization or imaging agent and the method comprises visualizing and/or imaging the silica particles after the surface has been contacted with them,
- wherein the dye molecule and/or colored particles are selected from the group consisting of rhodamine B, rhodamine 6G, carbon black, titanium dioxide, magnetite, crystal violet, and methylene blue.

16. The method according to claim 15 further comprising applying the agent as a dusting agent or as a suspension to the area.

17. The method according to claim 15, wherein the silica particles comprise a magnetic or paramagnetic particle that allows the agent to be applied to the area using a magnetic applicator.

18. The method according to claim 15, wherein the silica particles are microparticles having an average diameter of from about 10 to about 90 μm, optionally from about 45 to about 65 μm and further optionally from about 65 to about 90 μm.

19. A method for detecting a hydrophobic mass, comprising:
- contacting an area comprising a hydrophobic mass with an agent comprising hydrophobic silica particles, wherein the silica particles comprise a dye and/or colored particles, and wherein the silica particles comprise a magnetic or paramagnetic particle that allows the agent to be applied to the area using a magnetic applicator; and
- detecting, based upon the step of contacting an area, that the area contains the hydrophobic mass, the hydrophobic mass comprising a hydrophobic deposit.

20. The method according to claim 19, wherein the silica particles are obtained by a method in which the magnetic and/or paramagnetic particle are included in the mixture of the monomers and the hydrolysing agent and are thereby incorporated into the hydrophobic silica particles.

21. The method according to claim 19, wherein the magnetic or paramagnetic particle comprises haematite, titanium dioxide, carbon black or magnetite.

22. The method according to claim 19, further comprising visualizing the hydrophobic mass using an optical method.

23. The method according to claim 22, wherein the optical method is selected from the group consisting of a UV search light, an optical scanner including a flat-bed optical scanner, a fluorescent scanner and a UV visible scanner.

24. The method according to claim 19, wherein the silica particles are microparticles having an average diameter of from about 10 to about 90 μm, optionally from about 45 to about 65 μm and further optionally from about 65 to about 90 μm.

25. A method for detecting a hydrophobic mass, comprising:
- contacting an area comprising a hydrophobic mass with an agent comprising hydrophobic silica particles, wherein the silica particles comprise a dye and/or colored particles; and
- detecting, based upon the step of contacting an area, that the area contains the hydrophobic mass, the hydrophobic mass comprising a hydrophobic deposit,
- wherein the silica particles are microparticles having an average diameter of from about 10 to about 90 μm, optionally from about 45 to about 65 μm and further optionally from about 65 to about 90 μm.

26. The method according to claim 25 further comprising applying the agent as a dusting agent or as a suspension to the area.

27. The method according to claim 25, wherein the silica particles comprise a magnetic or paramagnetic particle that allows the agent to be applied to the area using a magnetic applicator.

28. The method according to claim 25 further comprising visualizing the hydrophobic mass using an optical method.

29. The method according to claim 28, wherein the optical method is selected from the group consisting of a UV search light, an optical scanner including a flat-bed optical scanner, a fluorescent scanner and a UV visible scanner.

30. A method for detecting a hydrophobic mass, comprising:
- contacting an area comprising a hydrophobic mass with an agent comprising hydrophobic silica particles, wherein the silica particles comprise a dye and/or colored particles; and
- detecting, based upon the step of contacting an area, that the area contains the hydrophobic mass, the hydrophobic mass comprising a hydrophobic deposit,
- wherein the silica particles are nanoparticles having an average diameter of about 200 to about 900nm, optionally an average diameter from about 300 to about 600nm and further optionally an average diameter of about 400 to about 500nm.

31. The method according to claim 30, wherein the nanoparticles are contacted with the area in a liquid medium.

32. The method according to claim 30 further comprising visualizing the hydrophobic mass using an optical method, optionally wherein the optical method is selected from the group consisting of a UV search light, an optical scanner including a flat-bed optical scanner, a fluorescent scanner and a UV visible scanner.

33. The method according to claim 32, wherein the optical method is selected from the group consisting of a UV search light, an optical scanner including a flat-bed optical scanner, a fluorescent scanner and a UV visible scanner.

* * * * *

UNITED STATES PATENT AND TRADEMARK OFFICE
CERTIFICATE OF CORRECTION

| | |
|---|---|
| PATENT NO. | : 8,530,599 B2 |
| APPLICATION NO. | : 13/245011 |
| DATED | : September 10, 2013 |
| INVENTOR(S) | : Rowell |

It is certified that error appears in the above-identified patent and that said Letters Patent is hereby corrected as shown below:

In the Claims:
Column 21, Claim 15, Line 3:
Please correct "comprising a hydrophobic with an agent"
      to read -- comprising a hydrophobic mass with an agent --

Signed and Sealed this
Seventh Day of October, 2014

Michelle K. Lee
*Deputy Director of the United States Patent and Trademark Office*